United States Patent [19]

Strom

[11] Patent Number: 4,482,754
[45] Date of Patent: Nov. 13, 1984

[54] OXIDATION OF BIPHENOLS
[75] Inventor: Robert M. Strom, Midland, Mich.
[73] Assignee: The Dow Chemical Company, Midland, Mich.
[21] Appl. No.: 464,445
[22] Filed: Feb. 7, 1983
[51] Int. Cl.$^3$ .................. C07C 39/14; C07C 37/00
[52] U.S. Cl. .................................................. 568/730
[58] Field of Search ............... 568/730, 726, 716, 719
[56] References Cited
U.S. PATENT DOCUMENTS 3,306,875  2/1967  Haye .................................... 568/730
3,562,338  2/1971  Zaweski .............................. 568/730
4,098,830  7/1978  Rutledge ............................. 568/730
4,108,980  8/1978  Rutledge ............................. 568/730
4,238,627  12/1980 Reichle ............................... 568/730
4,354,047  10/1982 Strom ................................. 568/730

Primary Examiner—Werren B. Lone
Attorney, Agent, or Firm—Douglas N. Deline

[57] ABSTRACT

Substituted phenols are converted in high yields to substituted 4,4'-biphenols by reaction with a substituted 4,4'-diphenoquinone. The substituted 4,4'-diphenoquinone reactant is regenerated by oxidation of a portion of the substituted 4,4'-biphenol product.

13 Claims, No Drawings

OXIDATION OF BIPHENOLS

BACKGROUND OF THE INVENTION

The present invention relates to a process for preparing biphenols, and, more particularly, to a process whereby a substituted phenol is directly oxidized to the corresponding biphenol.

Biphenols have found wide utility as bactericides, chemical intermediates, copolymers and antioxidants. For example, biphenols, especially 2,2',6,6'-tetraalkyl-substituted 4,4'-biphenols are used to stabilize animal and vegetable fats and oils, gasoline, rubber compounds and the like. Moreover, 4,4'-biphenol, which can be prepared by dealkylation of substituted biphenol, especially 2,2',6,6'-tetratertiary butyl-4,4'-biphenol, is an excellent comonomer for use in preparation of various condensation polymers and copolymers.

In U.S. Pat. No. 4,238,627, a one-step process is disclosed wherein a phenol is contacted with up to a stoichiometric amount of oxygen in the presence of a catalytic amount of a base to prepare 4,4'-bis-(2,6-dihydrocarbylphenols) substantially free of quinones.

In U.S. Pat. No. 3,631,208, the process of reducing diphenoquinones by contacting with phenols is explained. The diphenoquinones were prepared by oxidative coupling of phenols in the presence of a catalyst, particularly an amine basic cupric salt complex.

In U.S. Pat. No. 3,562,338, a similar process is disclosed wherein a phenol is oxidatively coupled to form a diphenoquinone by contacting with oxygen in the presence of an alkali metal hydroxide catalyst and thereafter reducing the diphenoquinone by contacting with a phenol in the substantial absence of oxygen and recovering the biphenol product.

Previous processes have first prepared a diphenoquinone by oxidatively coupling a phenol. Disadvantageously the prior art processes have been unduly inefficient. In particular, these processes have been characterized by the evolution of large amounts of heat due to the highly exothermic nature of the process. This fact necessitates the use of expensive thermal transfer equipment and procedures in order to maintain the reaction under control. The problem is compounded by the necessity to employ elevated temperatures in order for the oxidative coupling process to proceed at an acceptable rate. Prior art processes have further required inordinately long reaction times due to the kinetic limitations of the coupling process and have been limited by concomitant formation of undesired isomers thereby lowering selectivities to the desired p,p'-biphenol product.

Finally, and most significantly, prior art processes have had associated therewith a significant risk of explosion in view of the combination of low molecular weight phenols of relatively high volatility with oxygen at elevated temperatures.

It would be desirable to provide an improved process for preparing biphenols operating at greater efficiencies. It would also be desirable to provide an improved process for preparing biphenols that provides a reduced risk of explosion. It would further be desirable to provide an improved process for preparing biphenols that operates at improved selectivities and in shortened reaction times.

SUMMARY OF THE INVENTION

According to the present invention, there is provided a continuous method of forming a substituted 4,4'-biphenol corresponding to the formula:

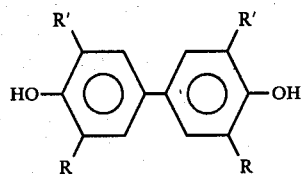

comprising:
(1) contacting a substituted 4,4'-biphenol corresponding to the formula:

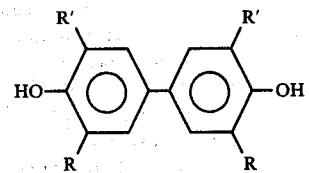

with oxygen in the presence of a catalytic amount of an oxidation catalyst to thereby prepare a substituted 4,4'-diphenoquinone corresponding to the formula:

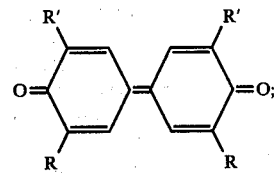

(2) reducing the substituted 4,4'-diphenoquinone by contacting with a 2,6-dialkylphenol corresponding to the formula:

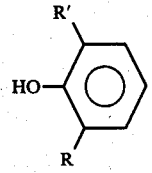

to thereby produce the substituted 4,4'-biphenol;
(3) recovering a portion of the substituted biphenol product; and
(4) recycling the remaining portion of the substituted biphenol product to step (1). In all the above formulas R is hydrogen or R', and R' is independently each occurrence a lower alkyl group.

DETAILED DESCRIPTION OF THE INVENTION

The present invention is characterized by high selectivities of formation of the desired p,p'-biphenol product, a vastly reduced heat load on the cooling means employed in the reactor and greatly increased margin of safety from explosion. Moreover, it has been found that compared to the direct coupling of phenolic compounds, the oxidation of substituted 4,4'-biphenols proceeds much more rapidly and requires substantially less catalyst, further contributing to the efficiency of the present process.

The first stage of the reaction is conducted at temperatures and pressures sufficient to obtain a reasonable reaction rate. Generally elevated temperatures are employed in order to achieve rapid reaction rates. Good oxidation results at temperatures from about 30° C. to about 300° C. Preferred temperatures are from about 50° C. to about 150° C. Pressures are suitably from about atmospheric to about 1000 psig. Preferably, pressures are from about 50 psig to about 500 psig.

The oxidant is oxygen which may be supplied as such or as a mixture of gases such as air. A preferred oxidant is air.

Solvents may be present if desired in order to aid in handling the reactants and products but the use of a solvent is not required for success of the process nor is it necessarily preferred. Generally, any organic solvent that is not itself subject to reaction under the present reaction conditions, e.g., inert, may be employed. Preferred solvents are aliphatic or aromatic hydrocarbons, alcohols, chlorinated hydrocarbons and alkyl phenols of up to about 20 carbons. Preferred solvents include toluene, diethylbenzene and t-butanol. Small amounts of water may additionally be present in any solvent mixture. The presence of water is, in fact, unavoidable since it is formed during the oxidation process.

The catalyst is any suitable oxidation catalyst or mixtures of such catalysts. Both heterogeneous or homogeneous catalysts may be employed. Suitable catalysts are bases, chelated metals, heterogeneous metal catalysts, etc.

Basic catalysts include alkali metal hydroxides or alkaline earth metal hydroxides, alkali metal salts of weak acids, alkaline earth metal salts of weak acids and amine bases.

Examples of chelated metal oxidation catalysts include activated copper, cobalt, manganese, nickel, chrome or iron complexes as taught, for example, by U.S. Pat. Nos. 3,631,208 and 4,098,830.

Heterogeneous metal catalysts are those comprised of active metals of group IIIB, IVB, VIB, VIIB, VIII, IB and IIB of the periodic table, tin and lead present in an oxidation state suitable to prepare the desired oxidation product. Of the heterogeneous metal catalysts, a noble metal-containing catalyst is preferred.

Preferred catalysts for the oxidation process are bases, especially the alkali metal hydroxides which are both inexpensive and highly effective due to the ease of oxidation of the biphenol reactant. The alkali metal hydroxide may be added as an aqueous mixture or as a solid.

The oxidation catalyst is present in a minor but effective amount. Generally, from about 0.01 mole percent to about 5 mole percent based on the amount of substituted biphenol reactant, and preferably from about 0.1 percent to about 1 percent of the catalyst is suitable.

After oxidation of the substituted 4,4'-biphenol reactant is substantially complete, the reaction is terminated. The reactor is cooled and the pressure is released if necessary. The substituted phenol reactant is then added to the reactor. It should be noted that one safety promoting feature of the present process is that large amounts of the substituted phenol are not present during the oxidation stage of the process. Preferably, the weight percentages of substituted phenol present in the first stage of the reaction is less than 10 percent, and most preferably less than 5 percent. This amount, if present, is due largely to the recycle of unreacted substituted phenol added during the second stage of the reaction. The reaction of the substituted phenol and the substituted 4,4'-diphenoquinone is conducted according to known processes such as those of U.S. Pat. Nos. 3,210,384; 3,306,874; 3,306,875 or 3,631,208, which teachings are incorporated herein by reference. Generally, the reaction proceeds readily upon merely heating the reaction mixture. The initial oxidation catalyst need not be removed during the subsequent reduction step. Certain compositions, especially bases or acids, are known to catalyze the coupling process. Accordingly, the preferred catalysts for the oxidation are those that additionally catalyze the coupling process, which catalysts are allowed to remain in the reaction mixture after completion of the oxidation step. For this reason, bases, especially alkali metal hydroxides, are preferred catalysts for the oxidation step as has been previously described. Temperatures from about 25° C. to about 100° C. are suitable. Generally the substituted phenol is employed in a molar amount of from about 2:1 to about 10.0:1 compared to the amount of substituted 4,4'-diphenoquinone.

When reduction of the substituted 4,4'-diphenoquinone is substantially complete, the reaction is terminated and the reaction mixture recovered. At this point a portion of the substituted biphenol product is recovered by any suitable means, most generally by selective precipitation or crystallization and removal of the desired portion of the product. Preferably, about one-half of the biphenol product is recovered. As an aid in recovering the desired portion of the biphenol product, a solvent or mixture of solvents may be employed to control the relativity solubility of the product in the reaction mixture. A particularly advantageous solvent for use with tertiary butyl-substituted biphenols is toluene. Accordingly, by adjusting the amount of solvent present or by reducing the solution temperature, some amount and preferably about one-half of the total substituted 4,4'-biphenol product is rendered insoluble and is easily separated from the reaction mixture. The remainder containing solvent, catalyst, substituted 4,4'-biphenol and unreacted substituted phenol is decanted or otherwise separated and recycled, optionally accompanied by a purification step, to the oxidation stage. The recovered product may be purified, if desired, by any suitable means.

Where it is desired to dealkylate the substituted 4,4'-biphenol product, especially 2,2',6,6'-tetratertiary butyl-4,4'-biphenol, the product may be contacted with a dealkylation catalyst such as an acid, suitably an organosulfonic acid. The dealkylation produces the desired 4,4'-biphenol and an olefin corresponding to the alkyl substituent, e.g., isobutylene in the case of tertiary butyl substituents.

While it may be seen that the process will work employing any substituted phenol corresponding to the formula provided, it is preferred that all substituents be identical alkyl groups. Most preferably, all substituents are tertiary alkyl groups.

SPECIFIC EMBODIMENTS

Having described the invention, the following example is provided as further illustrative of the invention and not to be construed as limiting.

EXAMPLE 1

A 300-ml stainless steel Parr Bomb is charged with 2,2',6,6'-tetratertiary butyl-4,4'-biphenol (5 g) toluene (30 ml), tertiary butyl alcohol (10 ml) and 20 percent aqueous NaOH (5 drops). The bomb is sealed, charged with oxygen and heated to 75° C. for one hour at a maximum pressure of 250 psig. Analysis of the reaction mixture by gas-liquid chromatography indicated an 85 percent conversion to 3,3',5,5'-tetratertiary butyl-4,4'-diphenoquinone.

The bomb is further charged with 2,6-ditertiary butyl phenol (5 g) and again sealed and heated to 75° C. for 3 hours. After reaction, the bomb is opened and the reaction contents removed. Upon cooling substantially pure 2,2',6,6'-tetratertiary butyl-4,4'-biphenol precipitates and is recovered. The supernatant liquid is recycled to the reactor to be oxidized.

What is claimed is:

1. A continuous process for preparing a substituted 4,4'-biphenol corresponding to the formula:

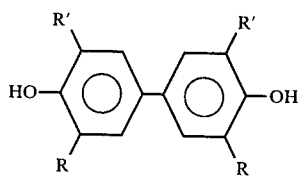

wherein R is hydrogen or R' and R' is independently each occurrence a lower alkyl group comprising:

(1) contacting a substituted 4,4'-biphenol corresponding to the formula:

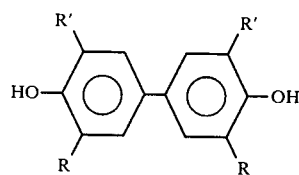

with oxygen at a temperature from about 30° C. to about 300° C. and a pressure from about atmospheric to about 1000 psig in the presence of a catalytic amount of an oxidation catalyst to thereby prepare a substituted 4,4'-diphenoquinone corresponding to the formula:

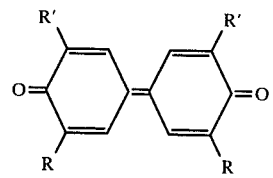

(2) reducing the substituted 4,4'-diphenoquinone by contacting with a substituted phenol corresponding to the formula:

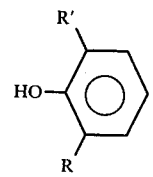

to thereby produce the substituted biphenol;
(3) recovering a portion of the substituted biphenol product; and
(4) recycling the remaining portion of the substituted biphenol product to step (1).

2. A process according to claim 1 wherein about one-half of the substituted biphenol product is recovered in step (3).

3. A process according to claim 1 wherein the substituted biphenol product is recovered by adjusting the relative solubility of the substituted biphenol product in the reaction mixture.

4. A process according to claim 1 wherein both R and R' are alkyl.

5. A process according to claim 4 wherein both R and R' are tertiary butyl.

6. A process according to claim 1 wherein the oxidation catalyst is a base, a chelated metal or a heterogeneous metal containing catalyst.

7. A process according to claim 6 wherein the catalyst is a base selected from the group consisting of alkali metal hydroxides, alkaline earth metal hydroxides, alkali metal salts of weak acids, alkaline earth metal salts of weak acids, amine bases and mixtures thereof.

8. A process according to claim 7 wherein the basic catalyst is an alkali metal hydroxide.

9. A process according to claim 1 wherein the temperature is from about 50° C. to about 150° C. and the pressure is from about atmospheric to about 500 psig.

10. A process according to claim 1 wherein the oxidant is air.

11. A process according to claim 1 wherein an inert organic solvent is additionally present.

12. A process according to claim 11 wherein the solvent is selected from the group consisting of aliphatic hydrocarbons, aromatic hydrocarbons, alcohols, chlorinated hydrocarbons, alkyl phenols of up to about 20 carbons, and mixtures thereof.

13. A process according to claim 12 wherein the solvent is toluene, diethylbenzene, t-butanol or a mixture thereof.

* * * * *